(12) United States Patent
Jones et al.

(10) Patent No.: US 8,534,117 B2
(45) Date of Patent: Sep. 17, 2013

(54) SENSOR APPARATUS AND METHOD THEREFOR

(75) Inventors: Beth A. Jones, Hook (GB); Paul Rennie, Bracknell (GB); Robert Pallant, Slough (GB); Paul D. Smith, Brighton (GB)

(73) Assignee: Kidde Technologies, Inc., Wilson, NC (US)

( * ) Notice: Subject to any disclaimer, the term of this patent is extended or adjusted under 35 U.S.C. 154(b) by 693 days.

(21) Appl. No.: 12/692,163

(22) Filed: Jan. 22, 2010

(65) Prior Publication Data

US 2011/0138880 A1 Jun. 16, 2011

(30) Foreign Application Priority Data

Dec. 14, 2009 (GB) .................................. 0921841.3

(51) Int. Cl.
*G01N 27/12* (2006.01)
(52) U.S. Cl.
USPC ....................................................... 73/31.06
(58) Field of Classification Search
USPC ....................................................... 73/31.06
See application file for complete search history.

(56) References Cited

U.S. PATENT DOCUMENTS

| | | | |
|---|---|---|---|
| 4,608,549 A | 8/1986 | Fukui | |
| 4,931,851 A | 6/1990 | Sibbald et al. | |
| 5,279,795 A | 1/1994 | Hughes et al. | |
| 5,849,165 A | 12/1998 | Kojima et al. | |
| 5,962,079 A * | 10/1999 | Koberstein et al. | ........... 427/508 |
| 6,012,327 A | 1/2000 | Seth et al. | |
| 6,499,335 B2 | 12/2002 | Nomura et al. | |
| 6,513,364 B1 | 2/2003 | Jonda et al. | |
| 7,156,967 B2 | 1/2007 | Hotta et al. | |
| 7,228,725 B2 | 6/2007 | Salter et al. | |
| 7,266,991 B2 | 9/2007 | Bley | |
| 7,321,287 B2 | 1/2008 | Ota et al. | |
| 7,479,255 B2 | 1/2009 | Otani et al. | |
| 7,491,547 B1 | 2/2009 | Warburton | |
| 2002/0142478 A1 | 10/2002 | Wado et al. | |
| 2006/0112756 A1 | 6/2006 | Xu | |
| 2006/0196246 A1 | 9/2006 | Li et al. | |
| 2006/0237316 A1 | 10/2006 | Clyde et al. | |
| 2007/0089989 A1 | 4/2007 | Hoagland | |

FOREIGN PATENT DOCUMENTS

| | | |
|---|---|---|
| CN | 2030379 | 1/1989 |
| CN | 1048770 | 1/1991 |
| CN | 101256163 | 9/2008 |
| DE | 10105581 | 11/2002 |

(Continued)

OTHER PUBLICATIONS

UK Search Report for GB0921841.3 dated Feb. 11, 2010.

(Continued)

*Primary Examiner* — Hezron E Williams
*Assistant Examiner* — Paul West
(74) *Attorney, Agent, or Firm* — Carlson, Gaskey & Olds, P.C.

(57) ABSTRACT

A sensor apparatus includes a metal oxide semiconductor ("MOS") sensor with a gas-sensing surface normally having a first sensitivity to a first species of flammable gas and a second sensitivity to a second, different species of flammable gas. A selective sensitivity-enhancement layer is disposed on the gas-sensing surface such that the first sensitivity becomes increased and the second sensitivity remains substantially unchanged.

18 Claims, 1 Drawing Sheet

(56) References Cited

FOREIGN PATENT DOCUMENTS

| EP | 1693667 | 8/2006 |
|---|---|---|
| JP | 122795 | 9/1989 |
| JP | 6148112 | 5/1994 |
| JP | 10170464 | 6/1998 |
| JP | 2006284327 | 10/2006 |

OTHER PUBLICATIONS

EP Search Report for EP10252032 dated Mar. 31, 2011.

* cited by examiner

SENSOR APPARATUS AND METHOD THEREFOR

RELATED APPLICATION

This application claims priority to GB Patent Application No. 0921841.3, which was filed Dec. 14, 2009.

BACKGROUND

This disclosure relates to a sensor apparatus for measuring a gas concentration in a surrounding environment.

Metal oxide semiconductor ("MOS") sensors and other types of sensors are known and used for detecting gas concentration levels. For instance, MOS sensors are cross-sensitive to a variety of different gases, including methane, hydrogen, ethanol, and isobutane.

SUMMARY

Disclosed is a sensor apparatus that includes a metal oxide semiconductor sensor with a gas-sensing surface normally having a first sensitivity to a first species of flammable gas and a second sensitivity to a second, different species of flammable gas. A selective sensitivity-enhancement layer is disposed on the gas-sensing surface such that the first sensitivity becomes increased and the second sensitivity remains substantially unchanged.

Also disclosed is a method of processing a sensor apparatus that includes forming the selective sensitivity-enhancement layer on the gas-sensing surface to increase the first sensitivity such that the second sensitivity remains substantially unchanged.

In another aspect, a sensor apparatus may include a metal oxide semiconductor sensor having a gas-sensing surface and a silicon-containing compound layer disposed on the gas-sensing surface.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
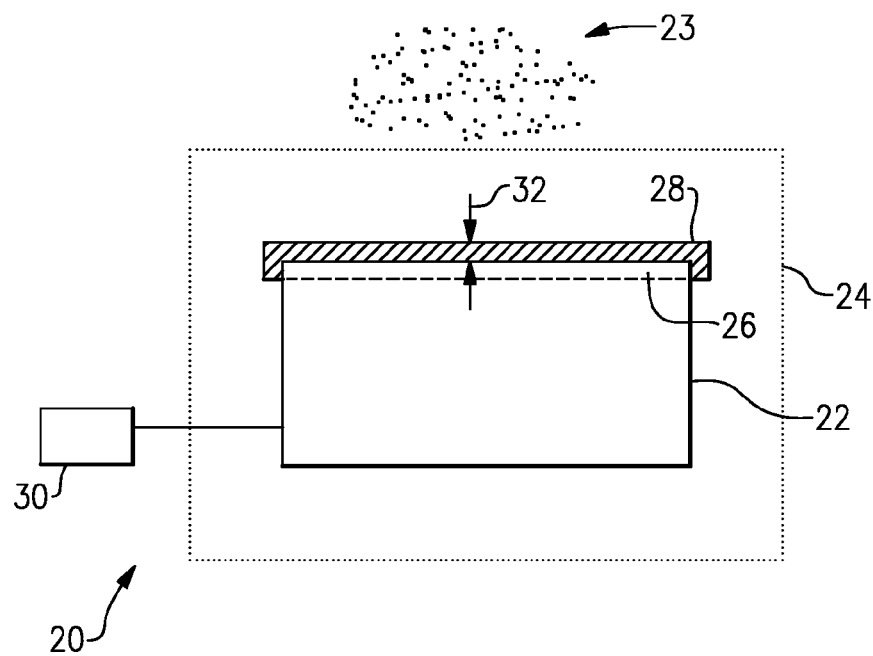
FIG. 1 illustrates an example sensor apparatus.

FIG. 1 illustrates selected portions of an example sensor apparatus 20 that is adapted to have increased sensitivity to a selected species of flammable gas, such as hydrogen. For instance, the sensor apparatus 20 may be used in an environment that may contain many different species of flammable gases. In the case of a vehicle (e.g., a commercial bus or other transportation device) that utilizes hydrogen for propulsion, enhanced hydrogen detection may be desired. Most metal oxide semiconductor ("MOS") sensors are typically more sensitive to other gases in the surrounding environment than to hydrogen, which can interfere with obtaining reliable hydrogen concentration measurements. However, as will be described, the sensor apparatus 20 is configured to have heightened sensitivity to hydrogen and may thereby be used to more reliably detect any hydrogen that escapes from hydrogen storage in a vehicle, for example.

In the illustrated example, the sensor system 20 includes a MOS sensor 22 (e.g., Figaro TGS2611) for sensing hydrogen or other target gas present in a surrounding atmosphere 23. As an example, the MOS sensor 22 may be enclosed within a housing 24 and the surrounding atmosphere may be considered to be the atmosphere outside of the housing 24. The MOS sensor 22 includes a gas-sensing surface 26 that interacts with target gas in a known manner to determine gas concentration in the surrounding atmosphere. The gas-sensing surface may be tin oxide ($SnO_2$), for example.

The sensor apparatus 20 further includes a selective sensitivity-enhancement layer 28 disposed on the MOS sensor 22. The selective sensitivity-enhancement layer 28 may be located immediately adjacent to and in contact with the gas-sensing surface 26.

The MOS sensor 22 may be electrically connected to a controller 30 for transmitting signals that are representative of detected gas concentrations. The controller 30 may include hardware, software, or both for receiving and processing the signals. As an example, the controller 30 may trigger an alarm or other indication in response to the received signals if the detected gas concentration exceeds a predetermined threshold.

The gas-sensing surface 26 normally (e.g., without the selective sensitivity-enhancement layer 28) has a first sensitivity to a first species of flammable gas and a second sensitivity to a second, different species of flammable gas. As an example, the flammable gases may be hydrogen and methane. The sensitivity may be represented by a voltage output of the MOS sensor 22, time for the MOS sensor 22 to reach 90% of a full scale output ($t_{90}$, for example), or any other suitable or known characteristic. In operation, the selective sensitivity-enhancement layer 28 increases sensitivity of the MOS sensor 22 to a first species of flammable gas (e.g., hydrogen) while the selective sensitivity-enhancement layer 28 does not substantially change the sensitivity of the MOS sensor 22 to a second species of flammable gas (e.g., methane). For instance, the sensitivity to the second species of flammable gas does not change by more than 6-10%. The sensitivity to the first species of flammable gas may increase by 20-70% and in some examples may increase by 40-70%. The selective sensitivity-enhancement layer 28 thereby increases the relative sensitivity of the MOS sensor 22 to hydrogen.

A thickness 32 of the selective sensitivity-enhancement layer 28 may be selected to achieve a desired enhancement. As an example, the thickness may be 0.5-100 micrometers. In a further example, the thickness may be 1-20 micrometers. For instance, using a thickness of under approximately 5 micrometers may provide a desirable enhancement of hydrogen sensitivity for vehicle end uses.

The selective sensitivity-enhancement layer 28 may be a silicon-containing compound layer, such as an oxide of silicon, formed from an organosilicon compound. In some examples, the organosilicon compounds may be in polymeric form, such as polydimethylsiloxane ("PDMS"), polydiethylsiloxane, polyalkylene oxide siloxane, phenylmethylsiloxane-dimethylsiloxane copolymer, diphenylsiloxane-dimethylsiloxane copolymer and combinations thereof.

The organosilicon compound may be mixed with a carrier liquid, such as ethanol, to form a solution. Other types of solvents may alternatively be used. The solution may then be deposited onto the gas-sensing surface 26. The ethanol or other carrier liquid facilitates depositing a uniform layer of the organosilicon compound onto the gas-sensing surface 26. In this regard, the organosilicon compound itself may be too viscous to readily deposit onto the gas-sensing surface 26 in a desired thickness. The carrier liquid thereby provides a viscosity that is more suitable for achieving a desired thickness.

After deposition of the solution, the carrier liquid evaporates such that the organosilicon compound remains on the gas-sensing surface 26. In this regard, using ethanol as the carrier liquid provides a suitable evaporation rate. In some cases, a high evaporation rate may lead to removal of the carrier liquid prior to uniform deposition. In other cases, lower evaporation rates may lengthen the process.

As an example, about 1-20 microliters per square millimeter of gas-sensing surface 26 may be deposited to control the thickness 32 to be within 1-20 micrometers. In a further example, about 2-8 microliters per square millimeter may be deposited. Multiple deposition cycles may be used to achieve a desired thickness.

After deposition of the solution and removal of the carrier liquid, the sensor apparatus 20 may be heated to remove any residual carrier liquid and oxidize the organosilicon compound into silicon-containing compound. The heat may be provided by operating the MOS sensor 22. Alternatively, the sensor apparatus 20 may be independently heated using a heating device. The sensor device 20 may be heated in an oxygen atmosphere, such as air, to oxidize the organosilicon compound to silicon-containing compound. In this regard, the selective sensitivity-enhancement layer 28 is a reaction product of the organosilicon compound. In some examples, the oxidation of the organosilicon compound forms silica (i.e., silicon dioxide) as the selective sensitivity-enhancement layer 28. The silicon dioxide may be β-quartz having a tetrahedron crystal structure. It is to be understood, however, that the type of silicon-containing compound formed may depend on the type of organosilicon compound that is selected, the temperature used to oxidize the organosilicon compound, and the atmosphere provided during oxidation. The selective sensitivity-enhancement layer 28 is therefore not limited to silicon dioxide and may include other types of silicon compounds.

Figure 2:
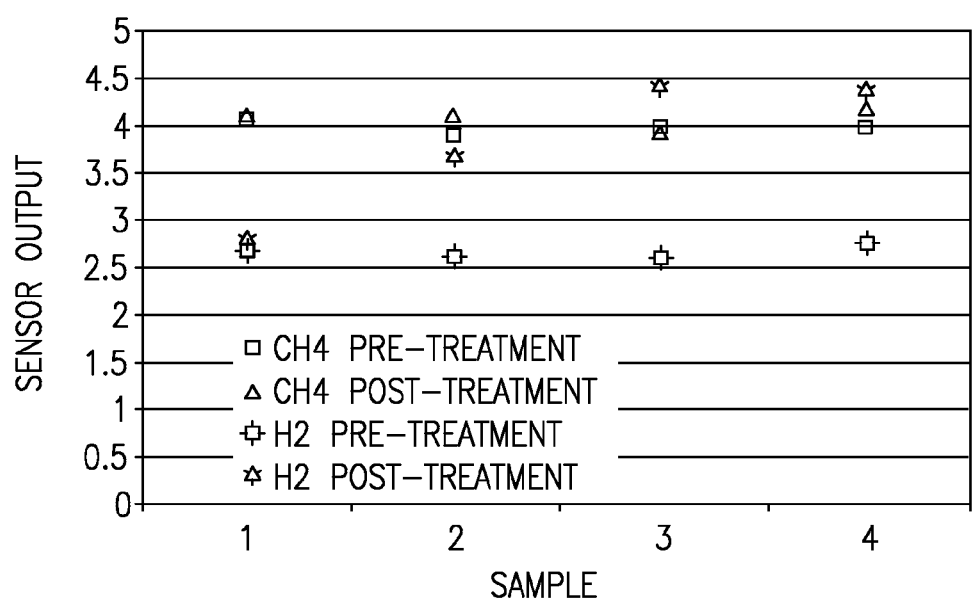
FIG. 2 graphically illustrates sensitivity of several sample sensors.

FIG. 2 graphically illustrates sensitivity to methane ($CH_4$) and hydrogen ($H_2$) of several sample MOS sensors, indicated as samples 1-4 (see Table 1). In this case, the sensitivity is represented as the full scale voltage output from the sample sensor when exposed to an atmosphere containing a 50% LEL (lower explosion limit) concentration of flammable gas, for example 2.5 vol % methane or 2 vol % hydrogen. The sensitivity of each sample 2-4 was determined without the selective sensitivity-enhancement layer 28 (pre-treatment) and with the selective sensitivity-enhancement layer 28 (post-treatment). For sample 1, pre-treatment and post-treatment are each without the selective sensitivity-enhancement layer 28.

TABLE 1

MOS Sensor Sensitivity Samples 1-4

| Sample No. | Post-treatment (deposition conditions) |
|---|---|
| 1 | None |
| 2 | Enhancement layer (5 microliter drop of 0.49 g PDMS in 150 ml ethanol resulting in 6 micrometer enhancement layer) |
| 3 | Enhancement layer (2 × 5 microliter drops of 0.49 g PDMS in 150 ml ethanol resulting in 12 micrometer enhancement layer) |
| 4 | Enhancement layer (3 × 5 microliter drops of 0.49 g PDMS in 150 ml ethanol resulting in 18 micrometer enhancement layer) |

Since the pre-treatment and post-treatment conditions of sample 1 are each without the selective sensitivity-enhancement layer 28, the sample 1 sensitivity does not substantially change between pre-treatment and post-treatment. The sensitivity of samples 2-4 for methane does not substantially change between pre-treatment and post-treatment. However, sensitivity of samples 2-4 for hydrogen increases between pre-treatment and post-treatment.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A sensor apparatus comprising:
   a metal oxide semiconductor ("MOS") sensor that includes a gas-sensing surface normally having a first sensitivity to a first species of flammable gas and a second sensitivity to a second, different species of flammable gas; and
   a selective sensitivity-enhancement layer disposed on the gas-sensing surface such that the first sensitivity is increased and the second sensitivity remains substantially unchanged, wherein the selective sensitivity-enhancement layer is a silicon-containing compound layer having a thickness of 1-20 micrometers.

2. The sensor apparatus as recited in claim 1, wherein the selective sensitivity-enhancement layer is silica.

3. The sensor apparatus as recited in claim 1, wherein the gas-sensing surface includes tin oxide.

4. The sensor apparatus as recited in claim 1, wherein the selective sensitivity-enhancement layer is located immediately adjacent to and in contact with the gas-sensing surface.

5. The sensor apparatus as recited in claim 1, wherein the silicon-containing compound layer is β-quartz silicon dioxide having a tetrahedron crystal structure.

6. The sensor apparatus as recited in claim 1, wherein the thickness is less than 5 micrometers.

7. The sensor apparatus as recited in claim 1, wherein the substantially unchanged second sensitivity does not change by more than 10%.

8. The sensor apparatus as recited in claim 7, wherein the substantially unchanged second sensitivity does not change by more than 6%.

9. The sensor apparatus as recited in claim 7, wherein the first species of flammable gas is hydrogen and the second species of flammable gas is methane, and the second sensitivity to the methane is with respect to an atmosphere containing 2.5 vol % methane.

10. The sensor apparatus as recited in claim 9, wherein the silicon-containing compound layer is β-quartz silicon dioxide having a tetrahedron crystal structure.

11. A method for use with a sensor apparatus having a metal oxide semiconductor ("MOS") sensor that includes a gas-sensing surface having a first sensitivity to a first species of flammable gas and a second sensitivity to a second, different species of flammable gas, comprising:

forming a selective sensitivity-enhancement layer on the gas-sensing surface to increase the first sensitivity such that the second sensitivity does not change by more than 10%, including forming the selective sensitivity-enhancement layer to be a layer of silicon containing compound having a thickness of 1-20 micrometers.

12. The method as recited in claim 11, including forming the selective sensitivity-enhancement layer as a reaction product of an organosilicon compound selected from a group consisting of polydimethylsiloxane, polydiethylsiloxane, polyalkylene oxide siloxane, phenylmethylsiloxane-dimethylsiloxane copolymer, diphenylsiloxane-dimethylsiloxane copolymer, and combinations thereof.

13. The method as recited in claim 11, including depositing a uniform layer of a solution that includes an organosilicon compound and a carrier liquid, removing the carrier liquid, and oxidizing the organosilicon compound into a silicon containing compound.

14. The method as recited in claim 11, wherein the second sensitivity does not change by more than 6%.

15. A sensor apparatus comprising:
a metal oxide semiconductor ("MOS") sensor having a gas-sensing surface; and
a silicon-containing compound layer disposed on the gas-sensing surface, wherein the silicon-containing compound layer is β-quartz silicon dioxide having a tetrahedron crystal structure.

16. The sensor apparatus as recited in claim 15, wherein the silicon-containing compound layer is a reaction product of an organosilicon compound selected from a group consisting of polydimethylsiloxane, polydiethylsiloxane, polyalkylene oxide siloxane, phenylmethylsiloxane-dimethylsiloxane copolymer, diphenylsiloxane-dimethylsiloxane copolymer, and combinations thereof.

17. The sensor apparatus as recited in claim 15, wherein the gas-sensing surface includes tin oxide and the silicon-containing compound layer has a thickness of 1-20 micrometers.

18. The sensor apparatus as recited in claim 15, wherein the silicon-containing compound layer is located immediately adjacent to and in contact with the gas-sensing surface.

* * * * *